United States Patent
Kaneko et al.

(10) Patent No.: US 10,660,915 B2
(45) Date of Patent: May 26, 2020

(54) METHOD FOR INDUCTION OF T CELLS FROM PLURIPOTENT STEM CELLS

(71) Applicant: KYOTO UNIVERSITY, Kyoto-shi, Kyoto (JP)

(72) Inventors: Shin Kaneko, Kyoto (JP); Atsutaka Minagawa, Kyoto (JP); Yutaka Yasui, Kyoto (JP)

(73) Assignee: Kyoto University, Kyoto-shi, Kyoto (JP)

( * ) Notice: Subject to any disclaimer, the term of this patent is extended or adjusted under 35 U.S.C. 154(b) by 0 days.

(21) Appl. No.: 15/526,294

(22) PCT Filed: Nov. 13, 2015

(86) PCT No.: PCT/JP2015/081959
§ 371 (c)(1),
(2) Date: May 11, 2017

(87) PCT Pub. No.: WO2016/076415
PCT Pub. Date: May 19, 2016

(65) Prior Publication Data
US 2017/0326175 A1  Nov. 16, 2017

(30) Foreign Application Priority Data
Nov. 13, 2014 (JP) .................. 2014-230355

(51) Int. Cl.
*A61K 35/14* (2015.01)
*C12N 5/10* (2006.01)
(Continued)

(52) U.S. Cl.
CPC .............. *A61K 35/14* (2013.01); *A61K 35/17* (2013.01); *C12N 5/0636* (2013.01);
(Continued)

(58) Field of Classification Search
None
See application file for complete search history.

(56) References Cited

U.S. PATENT DOCUMENTS

2009/0029463 A1  1/2009  Collins
2013/0078226 A1  3/2013  Nakauchi et al.

FOREIGN PATENT DOCUMENTS

| EP | 2853590 A1 | 4/2015 |
| WO | WO 2011/096482 A1 | 8/2011 |
| WO | WO 2013/176197 A1 | 11/2013 |

OTHER PUBLICATIONS

Deftos et al., Immunity 9: 777-786 (1998).*
(Continued)

*Primary Examiner* — Erin M. Bowers
(74) *Attorney, Agent, or Firm* — Knobbe, Martens, Olson & Bear, LLP

(57) ABSTRACT

The present invention provides a method for efficiently inducing CD8-positive T cells by adding vitamin C to the medium in the steps of induction of the CD8-positive T cells from pluripotent stem cells. The present invention also provides a method for efficiently inducing CD8-positive T cells by performing culture in a medium supplemented with an adrenocortical hormone agent in the step of induction of the CD8-positive T cells from CD4/CD8 double-positive T cells.

15 Claims, 3 Drawing Sheets

(51) Int. Cl.
    A61K 35/17      (2015.01)
    C12N 5/0783     (2010.01)
    C12N 5/074      (2010.01)
    C12N 5/16       (2006.01)
    C12N 5/00       (2006.01)
(52) U.S. Cl.
    CPC .......... C12N 5/0696 (2013.01); C12N 5/10 (2013.01); C12N 5/163 (2013.01); C12N 5/00 (2013.01); C12N 2501/125 (2013.01); C12N 2506/11 (2013.01); C12N 2506/45 (2013.01)

(56) References Cited

OTHER PUBLICATIONS

Ashwell et al., Annu. Rev. Immunol. 18: 309-345 (2000).*
R. Holmes et al., "The OP9-DL1 System: Generation of T-Lymphocytes from Embryonic or Hematopoietic Stem Cells In Vitro", *Cold Spring Harbor Protocols*, vol. 4, No. 2, Feb. 2009, doi:10.1101/pdb.prot5156, pp. 1-12.
Extended European Search Report dated Jun. 19, 2018 for European Patent Application No. EP 15 859 306.1, which cites the above-identified references numbered 1-2, and which shares priority of Japanese Patent Application No. JP 2014-230355 with subject U.S. Appl. No. 15/526,294.
International Search Report for International Application No. PCT/JP2015/081959, dated Dec. 8, 2015, in 2 pages.
International Preliminary Report on Patentability and Written Opinion of the International Searching Authority for International Application No. PCT/JP2015/081959, dated May 26, 2017, in 7 pages.
Berki et al., "Glucocorticoid (GC) sensitivity and GC receptor expression differ in thymocyte subpopulations," *International Immunology*, vol. 14(5), pp. 463-469 (2002).
Gattinoni et al., "Adoptive immunotherapy for cancer: building on success," *Nat Rev Immunol.*, vol. 6(5), pp. 383-393 (May 2006).
Huijskens et al., "Technical Advance: Ascorbic acid induces development of double-positive T cells from human hematopoietic stem cells in the absence of stromal cells," *Journal of Leukocyte Biology*, vol. 96(6), pp. 1165-1175 (Dec. 2014).
Ikawa et al., "An Essential Developmental Checkpoint for Production of the T Cell Lineage," *Science*, vol. 329, pp. 93-96 (Jul. 2, 2010).
Morgan et al., "Cancer Regression in Patients After Transfer of Genetically Engineered Lymphocytes," *Science*, vol. 314( 5796), pp. 126-129 (Oct. 6, 2006).
Nishimura et al., "Generation of Rejuvenated Antigen-Specific T Cells by Reprogramming to Pluripotency and Redifferentiation," *Cell Stem Cell*, vol. 12(1), pp. 114-126 (Jan. 3, 2013).
Screpanti et al., "Steroid Sensitivity of Thymocyte Subpopulations During Intrathymic Differentiation. Effects of 17 β-Estradiol and Dexamethasone on Subsets Expressing T Cell Antigen Receptor or IL-2 Receptor," *The Journal of Immunology*, vol. 142(10), pp. 3378-3383 (May 15, 1989).
Takayama et al., "Generation of functional platelets from human embryonic stem cells in vitro via ES-sacs, VEGF-promoted structures that concentrate hematopoietic progenitors," *BLOOD*, vol. 111(11), pp. 5298-5306 (Jun. 1, 2008).
Timmermans et al., "Generation of T Cells from Human Embryonic Stem Cell-Derived Hematopoietic Zones," *The Journal of Immunology*, vol. 182(11), pp. 6879-6888 (2009).

* cited by examiner

METHOD FOR INDUCTION OF T CELLS FROM PLURIPOTENT STEM CELLS

CROSS-REFERENCE TO RELATED APPLICATIONS

This application is the U.S. National Phase under 35 U.S.C. § 371 of International Application PCT/JP2015/081959, filed Nov. 13, 2015, which claims priority to JP 2014-230355, filed Nov. 13, 2014.

TECHNICAL FIELD

The present invention relates to a method for producing CD4/CD8 double-positive T cells using a medium supplemented with vitamin C in the steps of producing CD4/CD8 double-positive T cells from pluripotent stem cells, and a method for producing CD8-positive T cells, comprising the step of culturing the CD4/CD8 double-positive T cells in a medium containing an adrenocortical hormone agent.

BACKGROUND ART

T cells play a central role in the immune system against foreign pathogens such as bacteria and viruses, and against abnormal cells such as cancer cells. It is thought that a decrease in the function of T cells due to various causes may lead to increased susceptibility to infection and development of cancer and the like. If replacement or regeneration of immune cells is possible in cases of such diseases, it may act as very effective means for amelioration of the disease state and improvement of a therapeutic effect on the diseases. In such replacement therapy of immune cells, replacement and regeneration of the function of T lymphocytes, which are responsible for cell-mediated immunity, have been strongly demanded. However, no effective therapeutic method has been established so far.

In replacement therapies of T lymphocytes that have been proposed, gene transfer of an antigen-specific T cell receptor (TCR) gene into various lymphoid cells is carried out to allow replacement and activation of specific immune reaction (Non-patent Documents 1 and 2). In these attempts, CD34-positive cells, which are bone marrow progenitor cells, naive T lymphocytes, and the like are used as the cells to be subjected to the gene transfer. However, these have a number of disadvantages such as low ability of ex-vivo self-renewal, low gene transfer efficiency, and difficulty in regulation of differentiation by gene transfer.

Replacement therapies using T lymphocytes induced from pluripotent stem cells such as iPS cells have also been proposed (Non-patent Document 3 and Patent Document 1). In the method for inducing T lymphocytes from pluripotent stem cells, (1) a step of inducing hematopoietic progenitor cells from pluripotent stem cells, (2) a step of inducing CD4/CD8 double-negative cells from the hematopoietic progenitor cells, (3) a step of inducing CD4/CD8 double-positive cells from the CD4/CD8 double-negative cells, and (4) a step of inducing T lymphocytes from the CD4/CD8 double-positive cells, have been proposed.

For the step (1), a method in which a net-like structure sac (ES-sac) is formed from pluripotent stem cells to produce hematopoietic progenitor cells is known (Non-patent Document 4), For the steps (2) and (3), methods in which culture is performed on an OP9-DL1 cell layer in a medium supplemented with IL-7 and Flt-3L are known (Non-patent Documents 5 and 6). For the step (4), a method in which culture is performed in a medium supplemented with an anti-CD3 antibody (OKT-3) and IL-2 is known.

However, the efficiencies of production of T lymphocytes from pluripotent stem cells in these methods are insufficient, and their improvement has been demanded.

PRIOR ART DOCUMENTS

Patent Document

Patent Document 1: WO 2011/096482

Non-Patent Documents

Non-patent Document 1: Gattinoni L, et al., Nat Rev Immunol. 6(5): 383-393, 2006
Non-patent Document 2: Morgan R A, et al., Science. 314(5796): 126-129, 2006
Non-patent Document 3: Nishimura T, et al., Cell Stem Cell. 12(1): 114-126, 2013
Non-patent Document 4: Takayama N, et al., Blood. 111 (11): 5298-5306, 2008
Non-patent Document 5: Timmermans F, et al., J Immunol. 6879-6888, 2009
Non-patent Document 6: Ikawa T, et al., Science, 329(5987): 93-96, 2010

SUMMARY OF THE INVENTION

An object of the present invention is efficient production of hematopoietic progenitor cells from pluripotent stem cells. Another object of the present invention is efficient production of CD8-positive T cells from CD4/CD8 double-positive T cells derived from hematopoietic progenitor cells obtained by this method.

In order to achieve the above objects, the present inventors carried out a search for substances that are effective for efficient induction of hematopoietic progenitor cells from pluripotent stem cells. As a result, the present inventors discovered that hematopoietic progenitor cells can be efficiently induced by performing culture in a medium supplemented with vitamin C in the steps of differentiation of pluripotent stem cells into the hematopoietic progenitor cells. Further, the present inventors carried out a search for substances that are effective for efficient induction of CD8-positive T cells from CD4/CD8 double-positive T cells. As a result, the present inventors discovered that CD8-positive T cells can be efficiently induced by performing culture in a medium supplemented with an adrenocortical hormone agent, thereby completed the present invention.

The present invention provides the following inventions.
[1] A method for inducing CD8-positive T cells from pluripotent stem cells, comprising the steps of:
(1) culturing the pluripotent stem cells in a medium supplemented with vitamin C to induce hematopoietic progenitor cells;
(2) culturing cells obtained in said Step (1) in a medium supplemented with vitamin C to induce CD4/CD8 double-positive T cells; and
(3) culturing cells obtained in said Step (2) in a medium supplemented with an adrenocortical hormone agent to induce CD8-positive T cells.
[2] The method according to [1], wherein, in the Step (3), the medium further contains vitamin C.
[3] The method according to [1] or [2], wherein said vitamin C is vitamin C phosphate.

[4] The method according to any one of [1] to [3], wherein the vitamin C is supplied to the medium every day.

[5] The method according to any one of [1] to [4], wherein, in said Step (1), the pluripotent stem cells are cultured on C3H10T1/2 cells.

[6] The method according to any one of [1] to [5], wherein said Step (1) is carried out under low oxygen conditions with an oxygen concentration of not more than 5%.

[7] The method according to any one of [1] to [6], wherein, in said Step (1), the medium further contains vascular endothelial growth factor (VEGF), Stem cell factor (SCF), and Flt3 Ligand (FLT63L).

[8] The method according to any one of [1] to [7], wherein, in said Step (2), the cells obtained in Step (1) are cultured on OP9-DL1 cells.

[9] The method according to any one of [1] to [8], wherein, in said Step (2), the medium further contains FLT-3L and interleukin (IL)-7.

[10] A method for inducing CD8-positive T cells, comprising the step of culturing CD4/CD8 double-positive T cells in a medium supplemented with an adrenocortical hormone agent.

[11] The method according to [10], wherein said adrenocortical hormone agent is dexamethasone.

[12] The method according to [10] or [11], wherein said medium further contains an anti-CD3 antibody, vitamin C, IL-2, and IL-7.

[13] The method according to [12], wherein said vitamin C is vitamin C phosphate.

[14] A method for inducing hematopoietic progenitor cells, comprising the step of culturing pluripotent stem cells in a medium supplemented with vitamin C.

[15] The method according to [14], wherein said vitamin C is vitamin C phosphate.

[16] The method according to [14] or [15], wherein the vitamin C is supplied to the medium every day.

[17] The method according to anti one of [14] to [16], wherein said step of culturing pluripotent stem cells is a step of culturing pluripotent stem cells on C3H10T1/2 cells.

[18] The method according to any one of [14] to [17], wherein said step of culturing pluripotent stem cells is carried out under low oxygen conditions with an oxygen concentration of not more than 5%.

[19] The method according to any one of [14] to [18], wherein said medium further contains VEGF, SCF, and FLT-3L.

Effect of the Invention

According to the present invention, efficient production of CD8-positive T cells from pluripotent stem cells is possible by addition of vitamin C to the medium. Further, according to the present invention, efficient production of CD8-positive T cells from CD4/CD8 double-positive T cells is possible by addition of an adrenocortical hormone agent to the medium. Thus, according to the present invention, CD8-positive T cells can be efficiently produced from pluripotent stem cells, and a therapeutic agent that activates the immune function, containing CD8-positive T cells derived from pluripotent stem cells can be provided.

EMBODIMENTS FOR CARRYING OUT THE INVENTION

Figure 1:
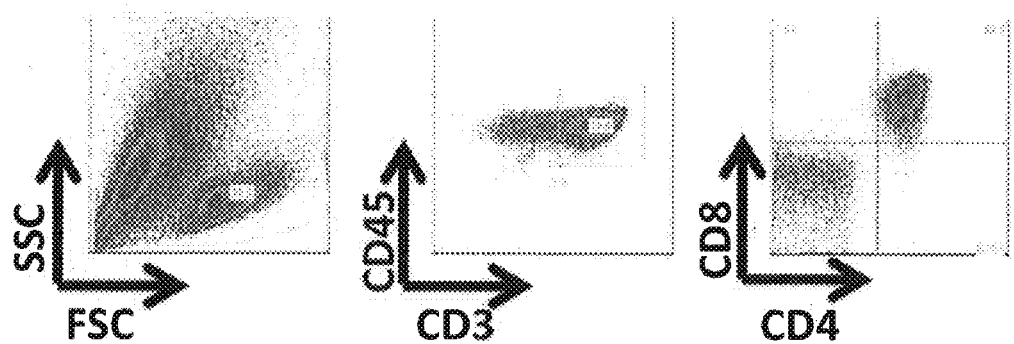
FIG. 1 shows the results of flow cytometry of cells cultured for 37 days. The left panel shows a diagram developed for FSC and SSC; the center panel shows a diagram developed for the staining intensities of CD3 and CD45; and the right panel shows a diagram developed for the staining intensities of CD4 and CD8.

The present invention provides a method for producing CD8-positive T cells from pluripotent stem cells. The production method can be divided into the steps of: (1) inducing hematopoietic progenitor cells from pluripotent stem cells; (2) inducing CD4/CD8 double-positive cells from the hematopoietic progenitor cells; and (3) inducing CD8-positive T cells from the CD4/CD8 double-positive cells.

Pluripotent Stem Cells

In the present invention, the pluripotent stem cells are stem cells having pluripotency that allows differentiation into many kinds of cells present in a living body, which stem cells also have the growth ability. The pluripotent stem cells at least include arbitrary cells which can be induced into the hematopoietic progenitor cells to be used in the present invention. Examples of the pluripotent stem cells include, but are not limited to, embryonic stem (ES) cells, embryonic step cells derived from a cloned embryo obtained by nuclear transfer (ntES cells), germline stem cells ("GS cells"), embryonic germ cells ("EG cells"), induced pluripotent stem (iPS) cells, and pluripotent cells derived from cultured fibroblasts or bone marrow stem cells (Muse cells). The pluripotent stem cells are preferably iPS cells from the viewpoint of the fact that these cells can be obtained without destroying embryos, eggs, or the like during the production process. The pluripotent stem cells are more preferably human iPS cells.

Methods for producing iPS cells are known in the art. These cells can be produced by introducing reprogramming factors into arbitrary somatic cells. Examples of the reprogramming factors herein include genes such as Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, and Glis1, and gene products thereof. These reprogramming factors may be used individually, or two or more of these may be used in combination. Examples of the combination of the reprogramming factors include those described in WO2007/069666, WO2008/118820, WO2009/007852, WO2009/032194, WO2009/058413, WO2009/057831, WO2009/075119, WO2009/079007, WO2009/091659, WO2009/101084, WO2009/101407, WO2009/102983, WO2009/114949, WO2009/117439, WO2009/126250, WO2009/126251, WO2009/126655, WO2009/157593, WO2010/009015, WO2010/033906, WO2010/033920, WO2010/042800, WO2010/050626, WO2010/056831, WO2010/068955, WO2010/098419, WO2010/102267, WO 2010/111409, WO2010/111422, WO2010/115050, WO2010/124290, WO2010/147395, WO2010/147612, Huangfu D, et al. (2008), Nat. Biotechnol., 26: 795-797, Shi Y, et al. (2008), Cell Stem Cell, 2: 525-528, Eminli S, et al. (2008), Stem Cells. 26: 2467-2474, Eluangfu D, et al. (2008), Nat. Biotechnol. 26: 1269-1275, Shi Y, et al. (2008), Cell Stem Cell, 3, 568-574, Zhao Y, et al. (2008), Cell Stem Cell, 3: 475-479, Marson A, (2008), Cell Stem Cell, 3, 132-135, Feng B, et al. (2009), Nat. Cell Biol. 11: 197-203, R. L. Judson et al., (2009), Nat. Biotechnol., 27: 459-461, Lyssiotis C A, et al. (2009), Proc Natl Acad Sci USA. 106: 8912-8917, Kim J13, et al. (2009), Nature. 461: 649-643, Ichida J K, et al. (2009), Cell Stem Cell. 5: 491-503, Heng J C, et al. (2010), Cell Stem Cell. 6: 167-74, Han J, et al. (2010), Nature. 463: 1096-100, Mali P, et al. (2010), Stem Cells. 28: 713-720, and Maekawa M, et al. (2011), Nature. 474: 225-9.

Examples of the somatic cells include, but are not limited to, any of fetal somatic cells, neonatal somatic cells, and healthy or diseased mature somatic cells, as well as any of primary cultured cells, subcultured cells, and established cell lines. Specific examples of the somatic cells include (1) tissue stem cells (somatic stem cells) such as neural stem cells, hematopoietic stem cells, mesenchymal stem cells, and dental pulp stem cells; (2) tissue progenitor cells; and (3) differentiated cells such as blood cells (peripheral blood cells, cord blood cells, and the like), lymphocytes, epithelial cells, endothelial cells, muscle cells, fibroblasts (skin cells and the like), hair cells, hepatic cells, gastric mucosal cells, enterocytes, spleen cells, pancreatic cells (pancreatic exocrine cells and the like), brain cells, lung cells, kidney cells, and adipocytes.

In the present invention, for use in the purpose of production of CD8-positive T cells, iPS cells are preferably produced by using, as somatic cells, lymphocytes (preferably T cell) that have undergone gene rearrangement of T cell receptor (TCR). In the present invention, in cases where lymphocytes are used, the reprogramming step is preferably carried out after activation of the lymphocytes by stimulation with an anti-CD3 antibody and an anti-CD28 antibody in the presence of interleukin-2 (IL-2). Such stimulation can be carried out by, for example, culturing the lymphocytes for a predetermined period in a medium supplemented with IL-2, the anti-CD3 antibody, and the anti-CD28 antibody.

The anti-CD3 antibody and the anti-CD28 antibody may be those to which magnetic beads or the like are bound. Instead of adding these antibodies to the medium, the T cells may be stimulated by culture on a culture dish having a surface to which the anti-CD3 antibody and the anti-CD28 antibody are bound. The stimulation may also be carried out by adding an antigen peptide that can be recognized by human T cells to the medium together with feeder cells.

The CD8-positive T cells produced in the present invention preferably has a desired antigen specificity. Thus, the lymphocytes as the origin of the iPS cells preferably have a desired antigen specificity, and the lymphocytes may be specifically isolated by purification using an affinity column or the like to which a desired antigen is immobilized. In this purification, a method in which lymphocytes having a desired antigen specificity are purified from a human tissue using a tetramer of MHC (major histocompatibility complex) (the so-called "MHC tetramer") to which a desired antigen is bound may also be employed.

In the present invention, the mammalian individual from which the somatic cells are derived is not limited. The mammalian individual is preferably human. In cases where CD8-positive T cells prepared by the present invention are used for blood transfusion, the somatic cells as the origin of the iPS cells are preferably isolated from the subject for which the blood transfusion of CD8-positive T cells is carried out, from the viewpoint of easily matching the type of the human leukocyte antigen (HLA) with that of the patient for which the blood transfusion is carried out.

Step of Inducing Hematopoietic Progenitor Cells from Pluripotent Stem Cells

In the present invention, hematopoietic progenitor cells (HPCs) are cells that are capable of differentiation into blood cells such as lymphocytes, eosinophils, neutrophils, basophils, erythrocytes, and megakaryocytes. In the present invention, hematopoietic progenitor cells and hematopoietic stem cells are not distinguished from each other, and regarded as the same kind of cells unless otherwise specified. The hematopoietic stem cells/progenitor cells can be recognized based on, for example, the positivity of CD34 and/or CD43, which are surface antigens.

In the present invention, the hematopoietic progenitor cells can be produced by a method comprising the step of culturing pluripotent stem cells in a medium supplemented with vitamin C.

In the present invention, "vitamin C" means L-ascorbic acid and derivatives thereof, and "L-ascorbic acid derivative" means derivatives that become vitamin C by enzymatic reaction in the living body. Examples of the derivatives of L-ascorbic acid include vitamin C phosphate, ascorbic acid glucoside, ascorbyl ethyl, vitamin C ester, ascorbyl tetrahexyldecanoate, ascorbyl stearate, and ascorbyl 2-phosphate 6-palmitate. The vitamin C is preferably vitamin C phosphate. Examples of the vitamin C phosphate include salts of L-ascorbic acid phosphate such as L-ascorbic acid phosphate Na and L-ascorbic acid phosphate Mg.

In the present invention, the medium to be used for the production of the hematopoietic progenitor cells is not limited. The medium may be prepared by adding vitamin C to a basal medium which is used for culture of animal cells. Examples of the basal medium include Iscove's Modified Dulbecco's Medium (IMDM), Medium 199, Eagle's Minimum Essential Medium (EMEM), αMEM medium, Dulbecco's modified Eagle's Medium (DMEM), Ham's F12 medium, RPMI 1640 medium, Fischer's medium, and Neurobasal Medium (Life Technologies), and mixtures of two or more of these media. The medium may contain serum, or may be serum-free. If necessary, the basal medium may also contain one or more of substances such as albumin, insulin, transferrin, selenium, fatty acid, trace elements, 2-mercaptoethanol, thiol glycerol, lipids, amino acids, L-glutamine, non-essential amino acids, vitamins, growth factors, low-molecular-weight compounds, antibiotics, antioxidants, pyruvic acid, buffers, inorganic salts, and cytokines.

The basal medium in the present invention is preferably IMDM medium containing serum, insulin, transferrin, selenium, thiol glycerol, L-glutamine, and ascorbic acid.

The medium o be used for the production of the hematopoietic progenitor cells in the present invention may be further supplemented with a cytokine(s) selected from the group consisting of BMP4 (Bone morphogenetic protein 4), VEGF (vascular endothelial growth factor), SCF (Stem cell factor), and FLT-3L (Flt3 Ligand). The medium is preferably a medium supplemented with VEGF, SCF, and FLT-3L.

In the present invention, the vitamin C is preferably added (supplied) every four days, every three days, every two days, or every day during the culture period. The vitamin C is more preferably added every day. The addition of the vitamin C to the medium is carried out at an amount corresponding to 5 ng/ml to 500 ng/ml. The amount is preferably an amount corresponding to 5 ng/ml, 10 ng/ml, 25 ng/ml, 50 ng/ml, 100 ng/ml, 200 ng/ml, 300 ng/ml, 400 ng/ml, or 500 ng/ml.

In the present invention, the concentration of the BMP4 in the medium to be used for the production of the hematopoietic progenitor cells is 10 ng/ml to 100 ng/ml, for example, 10 ng/ml, 20 ng/ml, 30 ng/ml, 40 ng/ml, 50 ng/ml, 60 ng/ml, 70 ng/ml, 80 ng/ml, 90 ng/ml, or 100 ng/ml. The concentration is preferably 20 ng/ml or 40 ng/ml.

In the present invention, the concentration of the VEGF in the medium to be used for the production of the hematopoietic progenitor cells is 10 ng/ml to 100 ng/ml, for example, 10 ng/ml, 20 ng/ml, 30 ng/ml, 40 ng/ml, 50 ng/ml, 60 ng/ml, 70 ng/ml, 80 ng/ml, 90 ng/ml, or 100 ng/ml. The concentration is preferably 20 ng/ml.

In the present invention, the concentration of the SCF in the medium to be used for the production of the hematopoietic progenitor cells is 10 ng/ml to 100 ng/ml, for example, 10 ng/ml, 20 ng/ml, 30 ng/ml, 40 ng/ml, 50 ng/ml, 60 ng/ml, 70 ng/ml, 80 ng/ml, 90 ng/ml, or 100 ng/ml. The concentration is preferably 30 ng/ml.

In the present invention, the concentration of the FLT-3L in the medium to be used for the production of the hematopoietic progenitor cells is 1 ng/ml to 100 ng/ml, for example, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 20 ng/ml, 50 ng/ml, or 100 ng/ml. The concentration is preferably 10 ng/ml.

In the production of the hematopoietic progenitor cells in the present invention, the pluripotent stem cells may be cultured by adherent culture or suspension culture. In cases of adherent culture, the culture may be carried out in a culture vessel coated with a coating agent, and/or may be co-cultured with other cells. Examples of the other cells for the co-culture include C3H10T1/2 (Takayama N., et al. J Exp Med. 2817-2830, 2010) and stromal cells derived from a different species (Niwa A et al. J Cell Physiol. 2009 November; 221(2): 367-77). Examples of the coating agent include Matrigel (Nivea A, et al. PLoS One. 6(7): e22261, 2011). Examples of the method of the suspension culture include the methods described in Chadwick et al. Blood 2003, 102: 906-15, Vijayaragavan et al. Cell Stem Cell 2009, 4: 248-62, and Saeki et al. Stem Cells 2009, 27: 59-67.

In the present invention, the hematopoietic progenitor cells can also be prepared from a net-like structure (which is also referred to as ES-sac or iPS-sac) obtained by culture of pluripotent stem cells. The "net-like structure" herein is a three-dimensional sac-shaped structure (having a space in the inside) derived from pluripotent stem cells. The structure is formed with an endothelial cell population or the like, and contains hematopoietic progenitor cells in the inside.

In the present invention, the temperature conditions for the culture for production of the hematopoietic progenitor cells are not limited. The temperature is, for example, about 37° C. to about 42° C., preferably about 37 to about 39° C. The culture period may be appropriately determined bye those skilled in the art by monitoring of the number of hematopoietic progenitor cells and/or the like. The number of days of the culture is not limited as long as hematopoietic progenitor cells can be obtained. Examples of the culture period include at least 6 days, not less than 7 days, not less than 8 days, not less than 9 days, not less than 10 days, not less than 11 days, not less than 12 days, not less than 13 days, and not less than 14 days. The culture period is preferably 14 days. A longer culture period is not problematic in the production of the hematopoietic progenitor cells. The culture may be carried out under low-oxygen conditions. Examples of the low-oxygen conditions in the present invention include 15%, 10%, 9%, 8%, 7%, 6%, 5%, and oxygen concentrations lower than these.

The culture for the production of the hematopoietic progenitor cells in the present invention can be carried out by appropriate combination of the above conditions. Examples of the combination include the steps of: (i) culturing pluripotent stem cells on C3H10T1/2 in a basal medium supplemented with vitamin C under low-oxygen conditions; and (ii) further adding VEGF, SCF, and FLT-3L to the culture liquid of (i), and culturing the cells under normal oxygen conditions. The period during which the step (i) is carried out is at least not less than six days, preferably not less than seven days, more preferably seven days. The period during which the step (ii) is carried out is at least not less than six days, preferably not less than seven days, more preferably seven days.

Step of Inducing CD4/CD8 Double-Positive T Cells from Hematopoietic Progenitor Cells In the present invention, "CD4/CD8 double-positive T cells" means T cells whose surface antigens CD4 and CD8 are both positive ($CD8^+CD4^+$). Since T cell can be recognized by the fact that their surface antigens CD3 and CD45 are positive, CD4/CD8 double-positive T cells can be identified as cells whose CD4, CD8, CD3, and CD45 are positive. CD4/CD8 double-positive T cells can be induced to differentiate into CD4-positive cells or CD8-positive cells.

In the present invention, the CD4/CD8 double-positive T cells can be produced by a method comprising the step of culturing hematopoietic progenitor cells in a medium supplemented with vitamin C.

In the present invention, the medium to be used for the production of the CD4/CD8 double-positive T cells is not limited. The medium may be prepared by adding vitamin C to a basal medium which is used for culture of animal cells. Examples of the basal medium include Iscove's Modified Dulbecco's Medium (IMDM), Medium 199, Eagle's Minimum Essential Medium (EMEM), αMEM medium, Dulbecco's modified Eagle's Medium (DMEM), Ham's F12 medium, RPMI 1640 medium, Fischer's medium, and Neurobasal Medium (Life Technologies), and mixtures of two or more of these media. The medium may contain serum, or may be serum-free. If necessary, the basal medium may also contain one or more of substances such as albumin, insulin, transferrin, selenium, fatty acid, trace elements, 2-mercaptoethanol, thiol glycerol, lipids, amino acids, L-glutamine, non-essential amino acids, vitamins, growth factors, low-molecular-weight compounds, antibiotics, antioxidants, pyruvic acrid, buffers, inorganic salts, and cytokines.

The basal medium to be used for production of the CD4/CD8 double-positive T cells in the present invention is preferably αMEM medium containing serum, transferrin, selenium, and L-glutamine. The vitamin C to be added to the basal medium is the same as that in the above-described induction of hematopoietic progenitor cells.

To the culture liquid to be used for the production of the CD4/CD8 double-positive T cells in the present invention, a cytokine(s) selected from the group consisting of FLT-3L and IL-7 may be further added. The medium is preferably a medium supplemented with FLT-3L and IL-7.

In the present invention, the concentration of the IL-7 in the medium to be used for the production of the CD4/CD8 double-positive T cells is 1 ng/ml to 50 ng/ml, for example, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 20 ng/ml, 30 ng/ml, 40 ng/ml, or 50 ng/ml. The concentration is preferably 5 ng/ml.

In the present invention, the FLT-3L can be used for the production of the CD4/CD8 double-positive T cells under the same conditions as described above.

In the production of the CD4/CD8 double-positive T cells in the present invention, the hematopoietic progenitor cells may be cultured by adherent culture or suspension culture. In cases of adherent culture, a coated culture vessel may be used, and/or the hematopoietic progenitor cells may be co-cultured with feeder cells and/or the like. Examples of the feeder cells for the co-culture include a bone-marrow stromal cell line, OP9 cells (available from Riken BioResource Center). The OP9 cells may be preferably OP-DL1 cells, which constantly express Dll1 (Holmes R1 and Zuniga-Pflucker J C. Cold Spring Harb Protoc. 2009(2)). In the present invention, in cases where OP9 cells are used as the feeder cells, Dll1, or a fusion protein of Dll1 and Fc or the like, separately prepared may be added to the medium to perform the co-culture. In the present invention, examples of the Dll1 include proteins encoded by a gene having the nucleotide sequence of the NCBI accession number NM #005618 in the case of human, or NCBI accession number NM #007865 in the case of mouse; and naturally occurring mutants having a high sequence identity (for example, having a sequence identity of not less than 90%) to these proteins and having an equivalent function. In cases where feeder cells are used for production of the CD4/CD8 double-positive T cells, the feeder cells are preferably appropriately replaced during the culture. The replacement of the feeder cells may be carried out by transferring the subject cells that are being cultured onto feeder cells that are preliminarily plated. The replacement may be carried out every five days, every four days, every three days, or every two days.

In the present invention, the culture temperature conditions for the culture of the hematopoietic progenitor cells for production of the CD4/CD8 double-positive T cells are not limited. The temperature is, for example, about 37° C. to about 42° C., preferably about 37 to about 39° C. The culture period may be appropriately determined by those skilled in the art by monitoring of the number of CD4/CD8 double-positive T cells and/or the like. The number of days of the culture is not limited as long as hematopoietic progenitor cells can be obtained. Examples of the culture period include at least not less than 10 days, not less than 12 days, not less than 14 days, not less than 16 days, not less than 18 days, not less than 20 days, not less than 22 days, and not less than 23 days. The culture period is preferably 23 days.

In the present invention, the CD4/CD8 double-positive T cells obtained may be isolated before use, or may be used as a cell population that also contains other cell species. In cases where the CD4/CD8 double-positive cells are isolated, the isolation may be carried out using any one index selected from the group consisting of CD4, CD8, CD3, and CD45. The isolation method may be a method well known to those skilled in the art, for example, a method in which the cells are labeled with a CD4, CD8, CD3, or CD45 antibody, and then isolated using a flow cytometer, or a method in which the cells are purified using an affinity column or the like to which a desired antigen is immobilized.

Step of Inducing CD8-Positive Cells from CD4/CD8 Double-Positive T Cells

In the present invention, the CD8-positive T cells means T cells whose surface antigen CD8 is positive (CD8$^+$CD4$^-$). These cells are also called cytotoxic T cells. Since T cell can be recognized by the fact that their surface antigens CD3 and CD45 are positive, CD8-positive cells can be identified as cells whose CD8, CD3, and CD45 are positive, while CD4 is negative.

In the present invention, the CD8-positive T cells can be produced by a method comprising the step of culturing CD4/CD8 double-positive T cells in a medium supplemented with an adrenocortical hormone agent.

The adrenocortical hormone agent to be used in the present invention is a glucocorticoid or a derivative thereof, and examples of the adrenocortical hormone agent include cortisone acetate, hydrocortisone, fludrocortisone acetate, prednisolone, triamcinolone, methylprednisolone, dexamethasone, betamethasone, and beclometasone dipropionate. The adrenocortical hormone agent is preferably dexamethasone.

In cases where the adrenocortical hormone agent is dexamethasone, its concentration in the medium is 1 nM to 100 nM, for example, 1 nM, 5 nM, 10 nM, 20 nM, 30 nM, 40 nM, 50 nM, 60 nM, 70 nM, 80 nM, 90 nM, or 100 nM. The concentration is preferably 10 nM.

In the present invention, the medium to be used for the production of the CD8-positive T cells is not limited. The medium may be prepared by adding an adrenocortical hormone agent to a basal medium which is used for culture of animal cells. Examples of the basal medium include Iscove's Modified Dulbecco's Medium (IMDM), Medium 199, Eagle's Minimum Essential Medium (EMEM), αMEM medium, Dulbecco's modified Eagle's Medium (DMEM), Ham's F12 medium, RPMI 1640 medium, Fischer's medium, and Neurobasal Medium (Life Technologies), and mixtures of two or more of these media. The medium may contain serum, or may be serum-free. If necessary, the basal medium may also contain one or more of substances such as albumin, insulin, transferrin, selenium, fatty acid, trace elements, 2-mercaptoethanol, thiol glycerol, lipids, amino acids, glutamine, non-essential amino acids, vitamins, growth factors, low-molecular-weight compounds, antibiotics, antioxidants, pyruvic acid, buffers, inorganic salts, and cytokines.

The basal medium in the present invention is preferably αMEM medium containing serum, transferrin, selenium, L-glutamine, and ascorbic acid.

In the present invention, the medium to be used for the production of the CD8-positive T cells preferably further contains an anti-CD3 antibody, vitamin C, and cytokine. Examples of the cytokine include IL-2 and IL-7. The cytokine to be used for the production of the CD8-positive T cells is preferably the combination of IL-2 and IL-7.

In the present invention, the CD3 antibody is not limited as long as it specifically recognizes CD3. Examples of the CD3 antibody include antibodies produced from OKT3 clone. The concentration of the CD3 antibody in the medium is 10 ng/ml to 1000 ng/ml, for example, 10 ng/ml, 50 ng/ml, 100 ng/ml, 200 ng/ml, 300 ng/ml, 400 ng/ml, 500 ng/ml, 600 ng/ml, 700 ng/ml, 800 rig/ml, 900 ng/ml, or 1000 ng/ml. The concentration is preferably 500 ng/ml.

In the present invention, the vitamin C can be used for the production of the CD8-positive T cells under the same conditions as described above.

In the present invention, the concentration of the IL-2 in the medium to be used for the production of the CD8-positive T cells is 10 U/ml to 1000 U/ml, for example, 10 U/ml, 20 U/ml, 30 U/ml, 40 U/ml, 50 U/ml, 60 U/ml, 70 U/ml, 80 U/ml, 90 U/ml, 100 U/ml, 500 U/ml, or 1000 U/ml. The concentration is preferably 100 U/ml.

In the present invention, the concentration of the IL-7 in the medium to be used for the production of the CD8-positive T cells is 1 ng/ml to 100 ng/ml, for example, 1 ng/ml, 5 ng/ml, 10 ng/ml, 20 ng/ml, 30 ng/ml, 40 ng/ml, 50 ng/ml, 60 ng/ml, 70 ng/ml, 80 ng/ml, 90 ng/ml, or 100 ng/ml. The concentration is preferably 10 ng/ml.

In the present invention, the culture temperature conditions for the culture of the CD4/CD8 double-positive T cells for production of the CD8-positive T cells are not limited. The temperature is, for example, about 37° C. to about 42° C., preferably about 37 to about 39° C. The culture period may be appropriately determined by those skilled in the art by monitoring of the number of CD8-positive T cells and/or the like. The number of days of the culture is not limited as long as CD8-positive T cells can be obtained. Examples of the culture period include at least not less than 1 day, not less than 2 days, not less than 3 days, not less than 4 days, or not less than 5 days. The culture period is preferably 3 days.

The present invention is described below more concretely by way of Examples. However, the scope of the present invention is not limited to these Examples.

Example 1

Cells iPS cells (TKT3v 1-7 line) were established using the method described in Nishimura T, et al., Cell Stem Cell, 12(1): 114-126, 2013 from human CD3-positive T cells isolated with informed consent.

C3H10T1/2 cells and OP9-DL1 cells were obtained from Riken BioResource Center.

Induction of CD4/CD8 Double-Positive T Cells

On confluent C3H10T1/2 cells in a 10-cm dish, a small cluster of the TKT3v 1-7 line was plated (Day 0), and the cells were cultured for seven days under low-oxygen conditions (5% $O_2$) in EB medium (IMDM supplemented with 15% fetal bovine serum (FBS), 10 μg/mL human insulin, 5.5 μg/mL human transferrin, 5 ng/mL sodium selenite, 2 mM L-glutamine, 0.45 mM α-monothioglycerol, and 50 μg/mL ascorbic acid) (Day 7).

Subsequently, 20 ng/mL VEGF, 30 rig/mL SCF, and 10 ng/mL FLT-3L (manufactured by Peprotech) were added, and culture was performed under normal oxygen pressure conditions for seven days (Day 14).

Hematopoietic cells contained in the resulting net-like structure (which is also referred to as iPS-SAC) ($CD34^+$ hematopoietic stem/progenitor cells) were collected, and then plated on OP9-DL1 cells. The cells were then cultured in OP9 medium (αMEM supplemented with 15% FBS, 2 mM L-glutamine, 100 U/ml penicillin, 100 ng/ml streptomycin, 5.5 μg/mL human transferrin, and 5 ng/mL sodium selenite) supplemented with 10 ng/mL FLT-3L and 5 ng/mL IL-7 under normal oxygen pressure conditions for 23 days (Day 37). The cells were plated onto fresh OP9-DL1 cells every 3 to 4 days.

During the culture period from Day 0 to Day 37, L-ascorbic acid 2-phosphate sesquimagnesium salt was added every day to a final concentration of 50 ng/ml.

On Day 37, CD3(+) CD45(+) CD4(+) CD8(+) fraction cells were isolated using FACS, to obtain CD4/CD8 double-positive cells (which are referred to as DP cells) (FIG. 1).

Differentiation Induction from CD4/CD8 Double-Positive Cells

Figure 2:
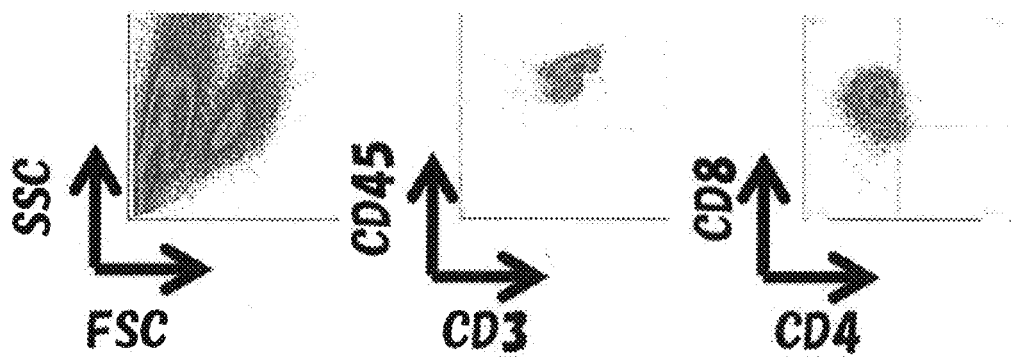
FIG. 2 shows the results of flow cytometry of cells obtained by culture of CD4/CD8 double-positive T cells for 3 days. The left panel shows a diagram developed for FSC and SSC; the middle panel shows a diagram developed for the staining intensities of CD3 and CD45; and the right panel shows a diagram developed for the staining intensities of CD4 and CD8.

DP cells obtained by the above method were plated on a 24-well plate, and cultured for three days in αMEM supplemented with 500 ng/ml anti-CD3 antibody (OKT3), 10 nM Dexamethasone (DEXART R, Fuji Pharma), 15% FBS, 2 mM L-glutamine, 100 U/ml penicillin, 100 ng/ml streptomycin, 5.5 μg/mL human transferrin, 5 ng/mL sodium selenite, 50 ng/ml L-ascorbic acid 2-phosphate, non-essential amino acid, 100 U/ml IL-2, and 10 ng/ml IL-7. As a result of investigation of the resulting cells using FACS, the cells was confirmed to be CD3(+) CD45(+) CD4(−) CD8(+) fraction cells (FIG. 2).

Example 2

Cells iPS cells (GPC3 line) were established using the method described in Nishimura T, et al., Cell Stem Cell. 12(1): 114-126, 2013 from human CD3-positive T cells isolated with informed consent. The human CD3-positive cells used are CD8-positive killer T cells, and have T cell receptor specific to the GPC3 antigen, whose expression in hepatoma is known.

Induction of CD8-Positive Cells Through CD4/CD8 Double-Positive T Cells on Feeder Cells On C3H10T1/2 cells, a small cluster of the GPC3 line was plated, and the cells were cultured by the same method as in Example 1, to obtain CD4/CD8 double-positive cells. The resulting CD4/CD8 double-positive cells were cultured by the same method as in Example 1, to induce CD8-positive cells.

Evaluation of CD8-Positive Cells

Figure 3:
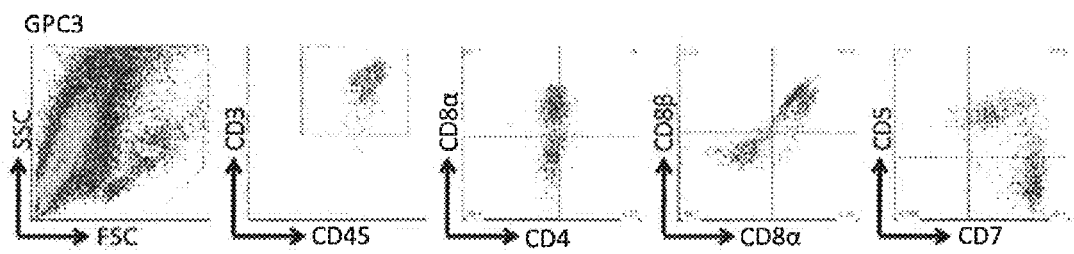
FIG. 3 shows the results of flow cytometry of cells obtained by culture of CD4/CD8 double-positive T cells induced from iPS cells (GPC line) for 3 days. Diagrams developed for FSC and SSC, for the staining intensities of CD3 and CD45, for the staining intensities of CD4 and CD8α, for the staining intensities of CD8α and CD8β, and for the staining intensities of CD5 and CD7 are shown.

The cell population induced from the GPC3 line by the above-described method was subjected to investigation of the expression of CD3, CD45, CD4, CD8α, CD8β, CD5, and CD7 using a flow cytometer. As a result, induction of CD8α/β double-positive CD8-positive cells could be confirmed (FIG. 3).

Figure 4:
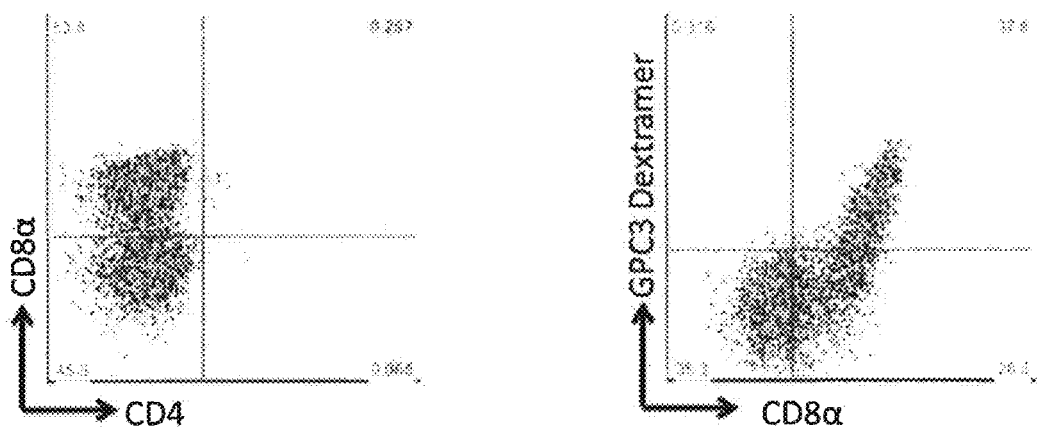
FIG. 4 shows the results of flow cytometry after bringing cells obtained by culture of CD4/CD8 double-positive 17 cells induced from iPS cells (GPC line) for 3 days into contact with GPC3 Dextramer. The left panel shows a diagram developed for the staining intensities of CD4 and CD8α, and the right panel shows a diagram developed for the staining intensities of GPC3 Dextramer and CD8α.
Figure 5:
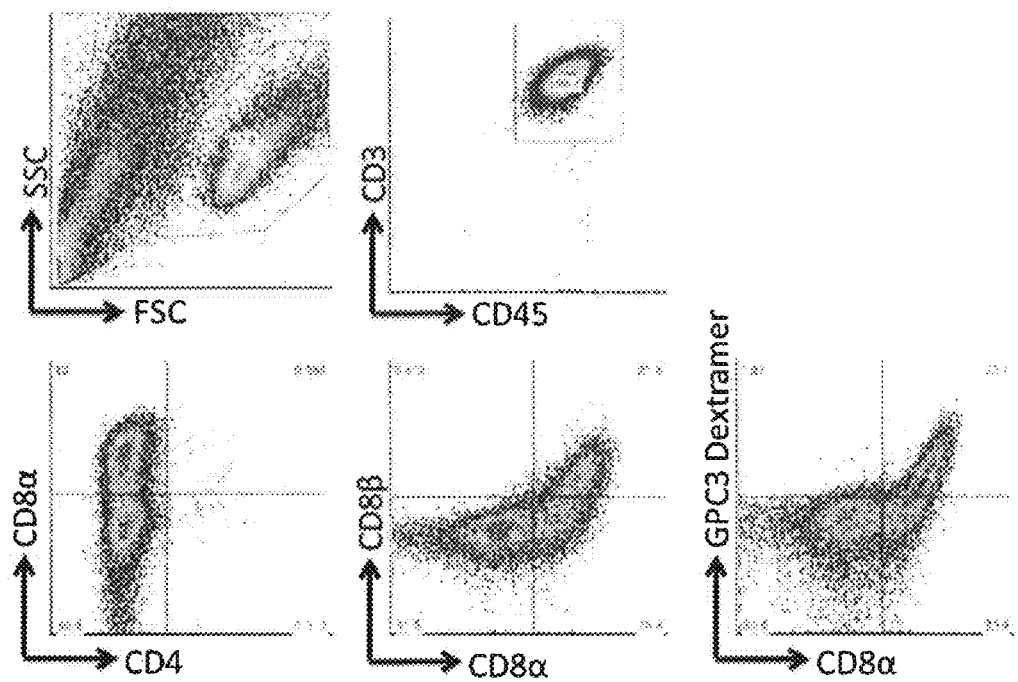
FIG. 5 shows the results of flow cytometry after bringing cells obtained by culture of CD4/CD8 double-positive T cells induced from iPS cells (GPC line) for 3 days into contact with GPC3 Dextramer. Diagrams developed for FSC and SSC, for the staining intensities of CD3 and CD45, for the staining intensities of CD4 and CD8α, for the staining intensities of CD8a and CAMP, and for the staining intensities of GPC3 Dextramer and CD8α are shown.

Further, GPC3 Dextramer (Immudex) was added to the resulting cells, and the reaction was allowed to proceed at 4° C. for 30 minutes, followed by adding CD3, CD45, CD4, and CD8α, antibodies thereto and performing analysis by flow cytometry. As a result, the CD8-positive cells obtained were found to be capable of specifically recognizing the Dextramer that is a complex of the MHC-GPC3 peptide (FIGS. 4 and 5).

Example 3

Cells iPS cells (4GAD 1-8 line) were established using the method described in Nishimura T, et al., Cell Stem Cell. 12(1): 114-126, 2013 from human CD3-positive T cells isolated with informed consent. The human CD3-positive cells used are CD4-positive helper T cells, and have T cell receptor specific to the GAD65 antigen, whose expression in pancreas is known.

Induction of CD8-Positive Cells Trough CD4/CD8 Double-Positive T Cells without Use of Feeder Cells A small cluster of the TKT3v 1-7 line or the 4GAD 1-8 line was plated on a 10-cm dish (Day 0), and the cells were cultured for seven days under low-oxygen conditions (5% $O_2$) in EB medium (IMDM supplemented with 15% fetal bovine serum (FBS), 10 µg/mL human insulin, 5.5 µg/mL human transferrin, 5 ng/mL sodium selenite, 2 mM L-glutamine, 0.45 mM α-monothioglycerol, and 50 µg/mL ascorbic acid) (Day 7).

Subsequently, 20 ng/mL VEGF, 30 ng/mL SCF, and 10 ng/mL FLT-3L (manufactured by Peprotech) were added, and culture was performed under normal oxygen pressure conditions for seven days (Day 14).

The cells were then cultured in OP9 medium (αMEM supplemented with 15% FBS, 2 mM L-glutamine, 100 U/ml penicillin, 100 ng/ml streptomycin, 5.5 µg/mL human transferrin, and 5 ng/mL sodium selenite) supplemented with 10 ng/mL 3L and 5 ng/mL IL-7 under normal oxygen pressure conditions for 23 days (Day 37).

During the culture period from. Day 0 to Day 37, L-ascorbic acid 2-phosphate sesquimagnesium salt was added every day to a final concentration of 50 ng/ml.

On Day 37, CD3(+) CD45(+) CD4(+) CD8(+) fraction cells were isolated using FACS, to obtain CD4/CD8 double-positive cells (which are referred to as DP cells) (FIG. 1).

The obtained DP cells were plated on a 24-well plate, and cultured for three days in αMEM supplemented with 500 ng/ml anti-CD3 antibody (OKT3), 10 nM Dexamethasone (DEXART R, Fuji Pharma), 15% FBS, 2 mM L-glutamine, 100 U/ml penicillin, 100 ng/ml streptomycin, 5.5 µg/mL human transferrin, 5 ng/mL sodium selenite, 50 ng/ml L-ascorbic acid 2-phosphate, non-essential amino acid, 100 U/ml IL-2, and 10 ng/ml IL-7.

Evaluation of CD8-Positive Cells

Figure 6:
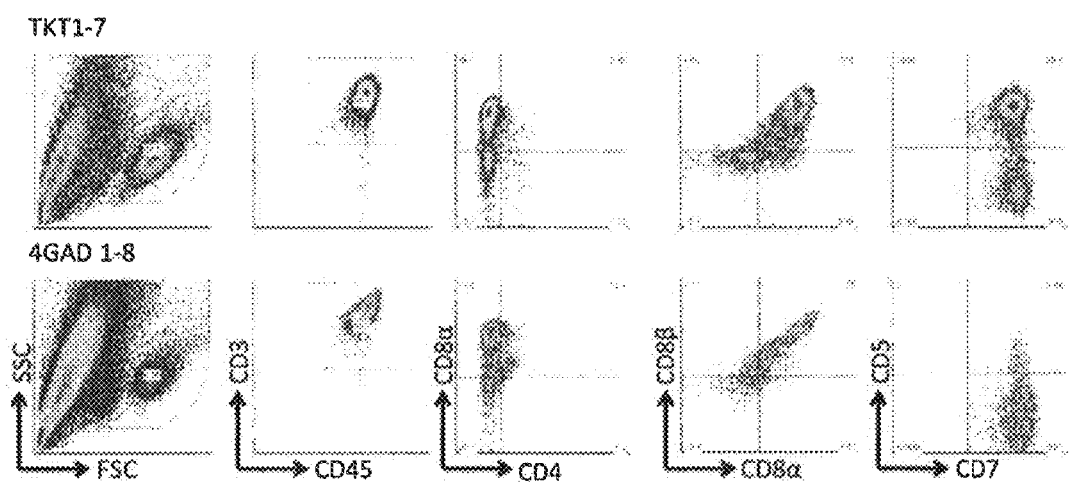
FIG. 6 shows the results of flow cytometry of cells obtained by culture of CD4/CD8 double-positive T cells produced from iPS cells (TKT3v 1-7 line and 4GAD 1-8 line) for 3 days without using feeder cells. Diagrams developed for FSC and SSC, for the staining intensities of CD3 and CD45, for the staining intensities of CD4 and CD8α, for the staining intensities of CD8α and CD8β, and for the staining intensities of CD5 and CD7 are shown.

The cell population induced from the GPC3 line by the above-described method was subjected to investigation of the expression of CD3, CD45, CD4, CD8α, CD8β, CD5, and CD7 using a flow cytometer. As a result, induction of CD8α/β double-positive CD8-positive cells could be confirmed (FIG. 6).

What is claimed is:

1. A method for inducing CD8-positive T cells, comprising the step of culturing CD4/CD8 double-positive T cells in a medium supplemented with an adrenocortical hormone agent and IL-7, wherein the adrenocortical hormone agent is glucocorticoid or a derivative thereof.

2. The method according to claim 1, wherein prior to said step of culturing the CD4/CD8 double-positive T cells in a medium supplemented with said adrenocortical hormone agent and interleukin (IL)-7, the method comprises the steps of:
(1) culturing pluripotent stem cells in a medium supplemented with vitamin C and vascular endothelial growth factor (VEGF) to induce hematopoietic progenitor cells; and
(2) culturing cells obtained in said Step (1) in a medium supplemented with vitamin C, FLT-3L and IL-7 to induce the CD4/CD8 double-positive T cells.

3. The method according to claim 2, wherein said vitamin C is vitamin C phosphate.

4. The method according to claim 2, wherein the vitamin C is supplied to the medium every day.

5. The method according to claim 2, wherein, in said Step (1), the pluripotent stem cells are cultured on C3H10T1/2 cells.

6. The method according to claim 2, wherein said Step (1) is carried out under low oxygen conditions with an oxygen concentration of not more than 5%.

7. The method according to claim 2, wherein, in said Step (1), the medium further comprises Stem cell factor (SCF), and Flt3 Ligand (FLT-3L).

8. The method according to claim 2, wherein, in said Step (2), the cells obtained in Step (1) are cultured on OP9-DL1 cells.

9. The method according to claim 1, wherein said adrenocortical hormone agent is dexamethasone.

10. The method according to claim 1, wherein said medium further comprises an anti-CD3 antibody, vitamin C, and IL-2.

11. The method according to claim 10, wherein said vitamin C is vitamin C phosphate.

12. The method according to claim 2, wherein, in said Step (1), the pluripotent stem cells are cultured on feeder cells.

13. The method according to claim 2, wherein, in said Step (2), the cells obtained in Step (1) are cultured on feeder cells.

14. The method according to claim 1, wherein said medium further contains a T cell stimulant.

15. The method according to claim 1, wherein the adrenocortical hormone agent is selected from the group consisting of cortisone acetate, hydrocortisone, fludrocortisone acetate, prednisolone, triamcinolone, methylprednisolone, dexamethasone, betamethasone, and beclometasone dipropionate.

* * * * *